(12) United States Patent
Kocifaj

(10) Patent No.: US 8,102,966 B2
(45) Date of Patent: Jan. 24, 2012

(54) RADIATION THERAPY WITH LOCAL FIELD ENHANCEMENT

(75) Inventor: Miroslav Kocifaj, Bratislava (SK)

(73) Assignee: Siemens Aktiengesellschaft, Munich (DE)

( * ) Notice: Subject to any disclaimer, the term of this patent is extended or adjusted under 35 U.S.C. 154(b) by 121 days.

(21) Appl. No.: 12/549,917

(22) Filed: Aug. 28, 2009

(65) Prior Publication Data

US 2011/0051890 A1    Mar. 3, 2011

(51) Int. Cl.
*A61N 5/10* (2006.01)
(52) U.S. Cl. .......................................... 378/65; 378/108
(58) Field of Classification Search .................. 378/65, 378/97, 108, 95
See application file for complete search history.

(56) References Cited

U.S. PATENT DOCUMENTS

2007/0280418 A1* 12/2007 Weil ................................ 378/65
2009/0296885 A1* 12/2009 Boeh et al. ...................... 378/65

OTHER PUBLICATIONS

Ning Sun: "X-Ray Raman Spectroscopy (XRS): Fundamentals and Applications"; Literature Seminar, Literature Seminar Advisor: Dr. Shane C. Street, Oct. 9, 2007, 151 Shelby Hall; Others; 2007.
E. Esam M. Khaled et al.: "Near-resonance excitation of dielectric spheres with plane waves and off-axis Gaussian beams"; Applied Optics, vol. 31, No. 9, Mar. 20, 1992, p. 1166-1169; Others; 1992.
Dipakbin Q. Chowdhury et al.: "Quality Factors and Effective-Average Modal Gain or Loss in Inhomogeneous Spherical Resonators: Application to Two-Photon Absorption" IEEE Journal of Quantum Electronics, vol. 29, No. 9, Sep. 1993, p. 2553-2561; Others; 1993.
Steven C. Hill et al.: "Morphology-dependent resonances associated with stimulated processes in microspheres"; Optical Society of America, vol. 3, No. 11, Nov. 1986, p. 1509-1514; Others; 1986.
Vladimier M. Shalaev: "Optical Nonlinearities of Fractal Composites," Optical Properties of Nanostructured Random Media; Topics in Applied Physics, vol. 82, p. 93-112, Springer-Verlag Berlin Heidelberg 2002, ISSN: 1437-0859; ISBN: 3-540-42031-2; Others; 2002; Germany.
Andrey K. Sarychev et al.: "Theory of Nonlinear Optical Responses in Metal-Dielectric Composites"; Optical Properties of Nanostructured Random Media, Topics Appl. Phys. 82, 169-184, Springer-Verlag Berlin Heidelberg 2002; Others; 2002.

* cited by examiner

*Primary Examiner* — Hoon Song
(74) *Attorney, Agent, or Firm* — Lempia Summerfield Katz LLC

(57) ABSTRACT

Aspects of the invention relate to radiotherapy methods and devices that use local field enhancements induced by metal particles in order to irradiate a target volume with a lower intensity as compared to conventional treatment methods. The metal particles may be coupled to vehicles and administered to a patient's body. As vehicles may have a higher affinity to the target volume than to the rest of the body, metal particles may concentrate within the target volume. When in irradiating the target volume, the metal particles cause local field enhancements of the treatment radiation, thus allowing irradiating the body with a lower overall intensity. Local field enhancements may be determined and used to control a radiation therapy device.

22 Claims, 4 Drawing Sheets

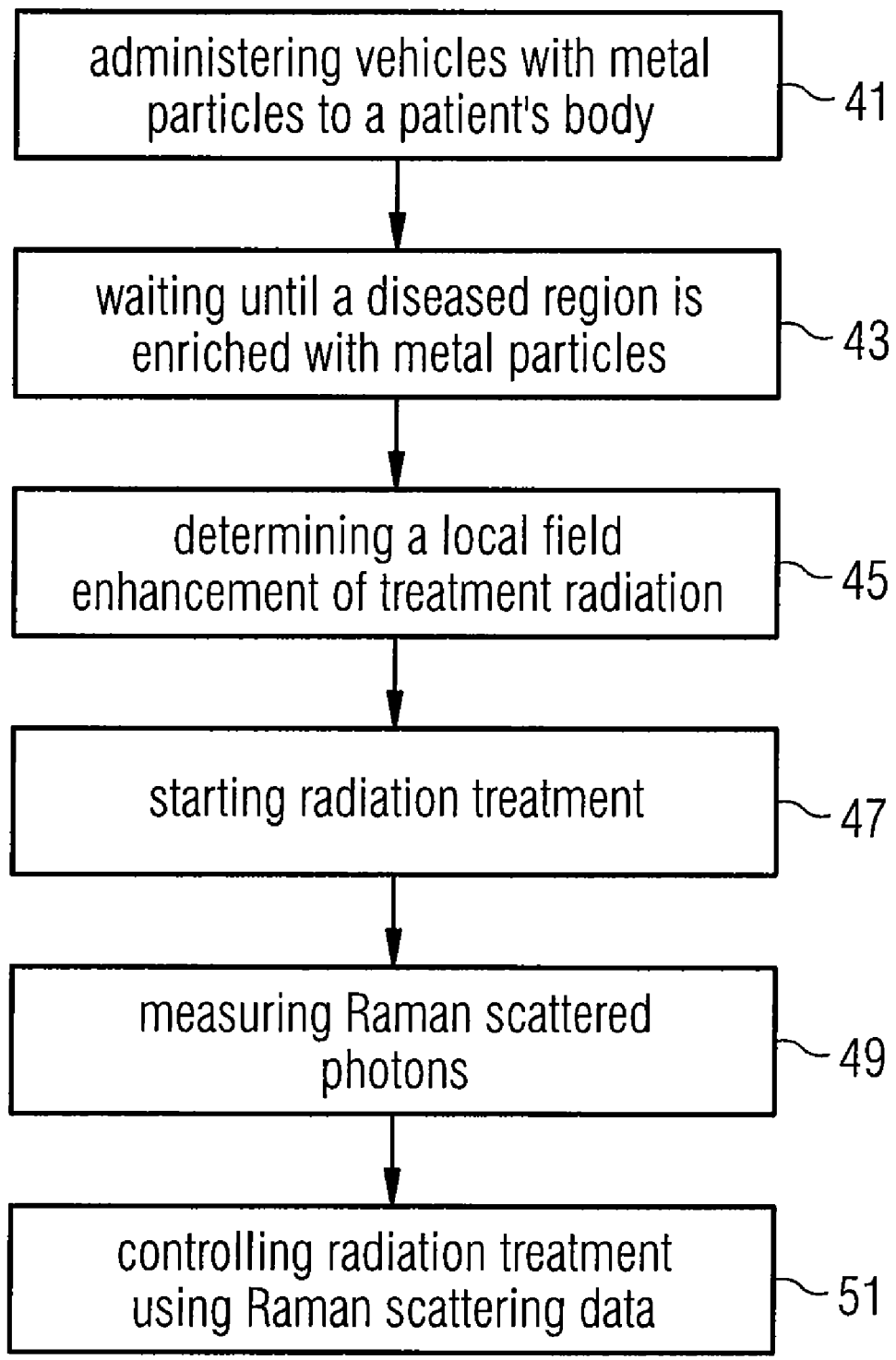

RADIATION THERAPY WITH LOCAL FIELD ENHANCEMENT

BACKGROUND

The following description relates to the field of radiotherapy, in particular to radiotherapy devices, radiotherapy treatment methods and computer software products used in this field.

Radiotherapy of radiation therapy is the treatment of cancer and other diseases with ionizing radiation. Ionizing radiation deposits energy that injures or destroys cells in the area subjected to the radiation by damaging their genetic material, making it impossible for these cells to continue to grow. Radiotherapy devices often use gamma radiation (or x-rays) for irradiating target cells. Unfortunately, the radiation damages both cancer cells and normal cells. Even if normal cells may have better cell repairing capabilities, damaging normal cells is one source of side effects that may occur during radiotherapy.

Alternatively or additionally, chemotherapy may be used to damage cancer cells by using chemicals, usually known as antineoplastic drugs. Chemotherapy influences the human body at a whole. As the chemotherapeutic drug remains within the body for a certain time after administration, side effects may arise even after chemotherapy has stopped.

SUMMARY

The present embodiments may obviate one or more of the drawbacks or limitations inherent in the related art.

For example, in a first aspect, a method of irradiating a human or animal body is provided. The method may include administering vehicles with metal particles to the human or animal body, the body having a diseased region that is to be irradiated with treatment radiation, the vehicles having a higher affinity to the diseased region than to a healthy region of the body, waiting until the diseased region is enriched with the metal particles, and applying treatment radiation to the diseased region.

Metal particles may be used to increase electromagnetic fields in the vicinity of the metal particles when the metal particles are irradiated by x-rays or gamma rays. These kinds of effects, also known as local field enhancement, were studied on metal particles and are described for example in Shalev V. M., "Topics in Applied Physics. Optical Properties of Nanostructured Random Media", Springer-Verlag, Berlin-Heidelberg, 2002, Volume 82.

Since the metal particles are embedded into the diseased region using the vehicles, irradiating the diseased region with treatment radiation, typically x-rays or gamma rays, results in an increase of the electromagnetic field of the incident radiation within the diseased region. This locally enhanced field has an intensity larger than the intensity of applied x-rays or gamma rays. Local field enhancement occurring in the vicinity of irradiated metal particles may reach high values; for example, they can be orders of magnitude higher than the incident x-rays or gamma rays. Therefore it is possible to damage cells within the diseased region efficiently, even if the applied incident treatment radiation has only a low intensity that would not be enough without the presence of metal particles.

In one embodiment, the local enhancement of the treatment radiation that is to be applied to the diseased region may be determined. This allows determining the strength of the electromagnetic field of the incident treatment radiation, such that the intensity of the incident radiation may be adjusted. For example, if the local enhancement of the treatment radiation would be too weak in order to irradiate the diseased region properly, the intensity of the incident treatment radiation may be increased until the local enhancement of the treatment radiation would be sufficient enough.

The local enhancement of the incident treatment radiation may be determined using information on size and concentration of the metal particles and on the wavelength of the treatment radiation. The intensity of the treatment radiation needed for inducing a certain effect within the diseased region may be calculated and automatically preselected for a given device setup.

In an embodiment, the method further includes inducing Raman scattered photons by applying radiation to the diseased region, detecting the Raman scattered photons and producing Raman scattering data, and controlling the treatment radiation based on the Raman scattering data. Under normal conditions without metal particles, Raman scattered photons are only induced to an extent that is not sufficient in order to be measurable. With the presence of metal particles, however, Raman scattered photons are induced due to local field enhancements in such intensity that Raman scattering becomes measurable and Raman scattered photons may be detected. This information may then be used to control the intensity of the treatment radiation, for example.

In an embodiment, predicted Raman scattering data may be generated. For example, the prediction value may indicate how much Raman scattering would be produced if treatment radiation would have been applied with a sufficient intensity. The predicted Raman scattering data may then be compared with the measured Raman scattering data. This information can be used to control treatment radiation. If the actual detected Raman scattering exceeds the prediction value, the intensity of the treatment radiation that is to be applied may be reduced. If the actual detected Raman scattering is lower than the prediction value, the intensity of the treatment radiation that is to be applied may be increased.

Using the measured Raman scattering data, the amount of local field enhancement within the diseased region may also be predicted and the treatment radiation that is to be applied may be adapted accordingly. For example, a prediction value may characterize the intensity of the treatment radiation that is induced by the metal particles within the diseased region. The prediction value may be compared with the desired value for treatment radiation within the diseased region and the radiotherapy may be controlled accordingly.

For example, when the prediction value is compared to the desired value, it may be determined that the prediction value exceeds the desired value. In this case, the intensity of treatment radiation emitted from the radiotherapy device may be reduced.

In a second aspect, a radiation therapy device is provided. The radiation therapy device may include a radiation source for producing treatment radiation, a radiation administering device for directing the treatment radiation to a diseased region of a patient, the diseased region of the patient being enriched with metal particles, a determining device for determining a value characterizing a local enhancement of the treatment radiation within the diseased region, the local enhancement being caused due to interaction of the treatment radiation with the metal particles, and a control device for controlling an administration of the treatment radiation directed to the patient, the controlling depending on the value.

The radiotherapy device, using the determining device for determining the value that characterizes the local field enhancement, may be controlled using the value in order to direct radiation to a diseased region of the patient enriched with metal particles. The total amount of the applied to radiation may be reduced compared to standard treatment when no metal particles are present in the diseased region.

Side effects caused by radiotherapy may therefore be reduced significantly. Compared to chemotherapy or to radiotherapy with radioactive substances administered to the body, the impact of the treatment of the patient's body disappears as the external radiation is switched off. Compared to conventional radiotherapy, intensity of treatment radiation applied to the patient's body may be significantly reduced.

In one embodiment, the determining device includes a calculation unit for calculating an intensity of the locally enhanced treatment radiation within the diseased region. The calculation may use information on the size of metal particles, on the concentration of metal particles in the region that is to be irradiated and on the wavelength of the treatment radiation directed to diseased region.

The controlled device may control a first intensity of the treatment radiation that is directed to the patient with the radiation administering device in order to induce the locally enhanced treatment radiation within the diseased region with a second intensity that exceeds a desired value.

In another embodiment, the determining device may include a Raman scattering detecting device for detecting Raman scattered photons, the Raman scattered photons originating from the irradiation of the metal particles in the diseased region with the treatment radiation, and for producing Raman scattering data. The Raman scattering data may represent the value characterizing the local enhancement of treatment radiation.

Under normal conditions, i.e., without the presence of metal particles, treatment radiation emitted from a radiotherapy device may stimulate Raman scattered photons only to an extent that is not sufficient for Raman scattered photons to become measurable. When treatment radiation is applied to a region enriched with metal particles, local enhancement of the applied electromagnetic field may stimulate Raman scattered photons sufficiently in order to make them measurable. Therefore, measuring the Raman scattered photons with the Raman scattering detecting device gives information about the local field enhancement. This allows concluding whether the region was sufficiently irradiated or not.

In an embodiment, an intensity of the treatment radiation emitted from the radiotherapy device and directed to the patient may be controlled based on the Raman scattering data.

Once the Raman scattering has been measured, the incident power of the treatment radiation may be adjusted. Compared to standard treatment without metal particles, the operating energies of the radiotherapy device may be reduced significantly. The whole radiotherapy treatment will affect less healthy regions in a patient's body and may be better tolerated. Nevertheless, at the same time, the electromagnetic field intensities induced in the diseased region doped by metal particles will still be very high, resulting, for example, in an efficient damage of tumor cells.

It may be possible to generate a prediction of Raman scattering data that should be measured when radiation is applied to the region enriched with metal particles. The prediction value of the Raman scattering data may then be compared to the actual measured from and scattering data when radiation is actually applied to the region. If the actual measured value for Raman scattering photons exceeds the prediction value, the overall intensity of the radiation applied to the region may be reduced. If the predicted Raman scattering data exceeds the actual measured Raman scattering data, the radiation applied to the region may be increased.

In an embodiment, the Raman scattering data may be used to determine a prediction value for the strength of the locally enhanced treatment radiation within the diseased region. The control device may be configured to adapt the strength of the treatment radiation directed from the radiotherapy device to the patient if the prediction value differs from a predetermined desired value.

BRIEF DESCRIPTION OF THE DRAWINGS

Embodiments are illustrated in the following figures.

FIG. 5 shows a schematic representation of a method for radiation therapy.

DETAILED DESCRIPTION

Figure 1:
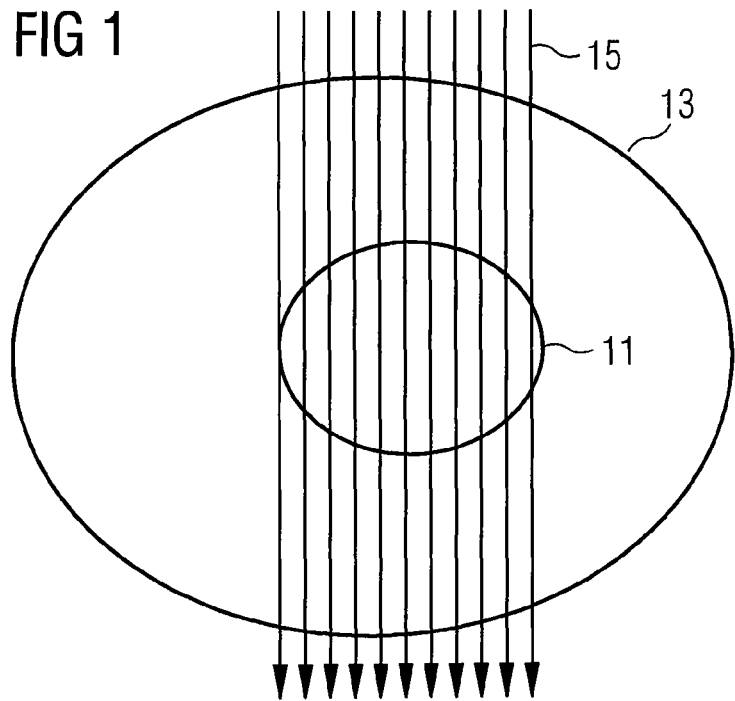
FIG. 1 shows schematically one embodiment of a conventional radiation treatment.

FIG. 1 shows the situation of a conventional radiation treatment. The target volume 11, for example, a tumor, is part of a patient's body 13. In order to irradiate the target volume 11 properly, x-ray or gamma ray radiation 15 is directed to the target volume 11 through the patient's body 13 with an intensity that is sufficient for irradiating the target volume 11 properly, for example, as defined in a treatment plan. The incident radiation 15 affects the target volume 11 and also surrounding structures.

Figure 2:
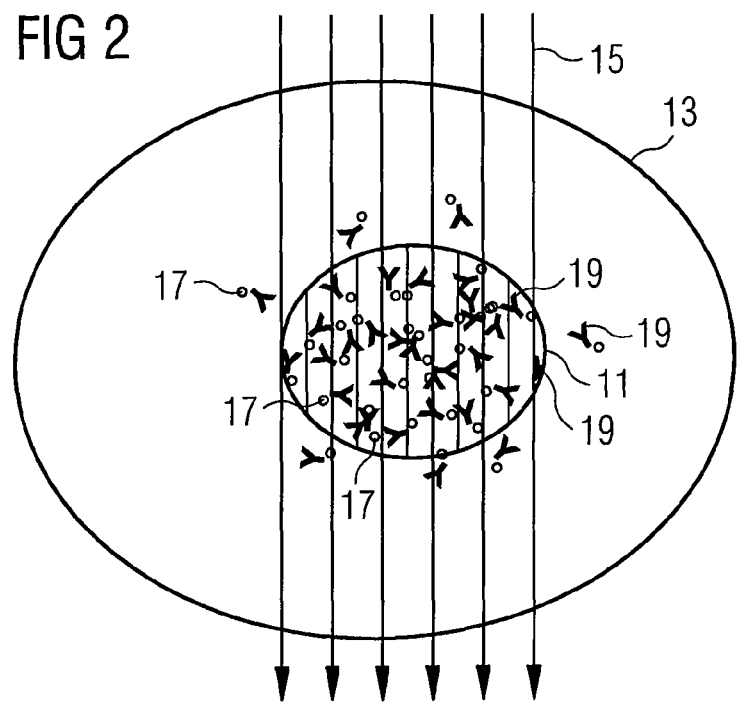
FIG. 2 shows schematically one embodiment of a radiation treatment, where the diseased region is enriched with metal particles.

FIG. 2 shows the target volume 11 enriched with small metal particles 17, such as small gold particles or gold grains. Gold is a suitable material for the metal particles, as gold is usually well tolerated by the patient's body 13.

The target volume 11 may be enriched with metal particles 11 using vehicles 19. If the region that is to be treated is, for example, a tumor, monoclonal antibodies are one possibility of such vehicles 19. Suitable monoclonal antibodies may recognize specific target structures on the surface of the tumor cell, e.g. a tumor specific protein. When one or more metal particles 17 are coupled to such a vehicle 19, the vehicles 19 may be administered to the body and after a certain amount of time the vehicles 19 with the metal particles 17 will have enriched within the tumor region, resulting in a higher concentration of metal particles within the tumor region than in other regions of the patient's body 13.

As the metal particles 17 locally enhance the field of the applied incident radiation 15, the target volume 11 may be irradiated with a lower intensity compared to standard treatment. Nevertheless the diseased region can be properly treated due to the local enhancement.

By using metal particles 17, it is possible to irradiate the body 13 with lower energies compared to standard radiotherapy without such metal particles 17, but to have tumor cells nevertheless damaged to a comparable extent. Furthermore, the effect of radiation is localized to the target volume 11. This allows inducing damages in tumor cells whereas other parts of the human body 13 will be affected only slightly.

The effect that abnormally increased local electromagnetic fields can be induced near metal particles 17 after they are irradiated by X-rays (or gamma rays) were studied and published for example in Shalev V. M. (Ed.) "Topics in Applied Physics. Optical Properties of Nanostructured Random Media," Springer-Verlag, Berlin-Heidelberg, 2002. Local resonances occurring in the vicinity of irradiated metal or gold particles 17 may be high, for example, the local resonances may be orders of magnitude higher than the incident field. The abnormal changes of electromagnetic field may occur due to size, refractive index or shape of the particles.

The mechanism for these enhanced local fields may be interference. For MDRs (for: "morphology dependent resonances") the resonances become sharper and higher for larger particles. MDRs have been described, for example, in Hill S C, Benner R E, "Morphology-dependent resonances associated with stimulated processes in microspheres", Journal of the Optical Society of America B, Vol. 3, No. 11. 1986, 1509-1513.

If the particles are roughly 10-times (or more than 10-times larger) the wavelength, then one can see this type of resonance with X-rays and nanospheres, but the nanospheres should be extremely round to see these resonances, see e.g. Chowdhury D Q, Hill S. C., Mazumder M M, "Quality factors and effective-average modal gain or loss in inhomogeneous spherical resonators: application to two-photon absorption", IEEE Journal of Quantum Electronics, Vol. 29, Issue 9, 1993, 2553-2561 and Khaled E E M et al., "Near-resonance excitation of dielectric spheres with plane waves and off-axis Gaussian beams", Applied Optics, Vol. 31, Issue 9, 1992, 1166-1169. These kinds of resonances decay rapidly when there is any irregularity.

For large spherical particles the enhanced electromagnetic fields occur due to resonance phenomenon, for example, when perimeter of the sphere to the wavelength is an integer value. One can have other shapes, like cylinders, ellipsoids, or even boxes, but then the enhancement is much weaker for these other particles.

Figure 3:
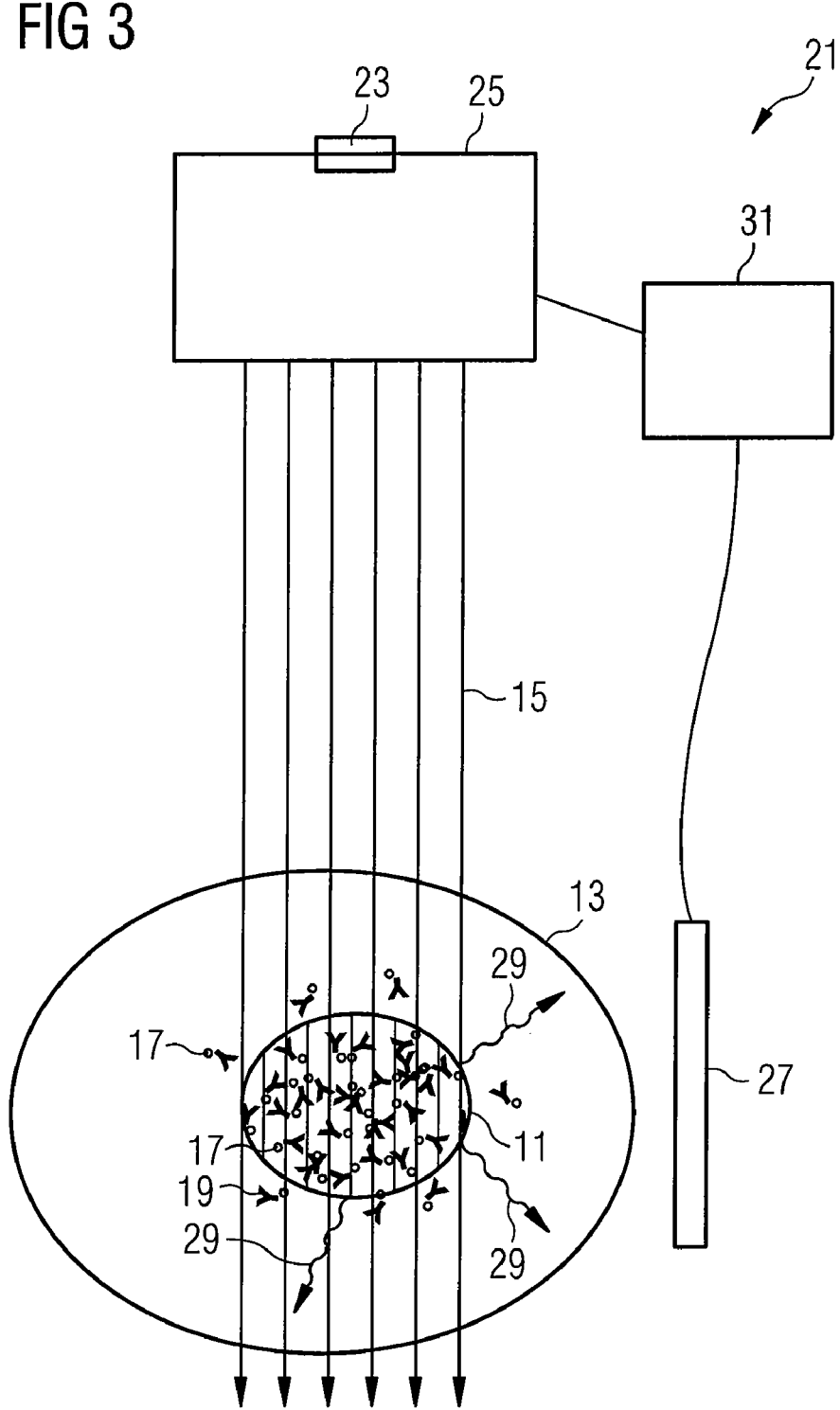
FIG. 3 shows schematically an embodiment of a radiotherapy device that can be used for an irradiation of a diseased region enriched with metal particles.

FIG. 3 shows a schematic drawing of an embodiment of a radiotherapy system 21 for treating a diseased region 11 enriched with metal particles 17. Other components, such as a patient table, a radiotherapy housing and other radiotherapy components, may be included in the radiotherapy system 21.

The radiotherapy device 21 has a radiation source 23 that is operable to produce treatment radiation 15.

The treatment radiation 15 produced the radiation source 23 may be modified with a radiation administering device 25 and directed to the patient's body 13. The radiation source 23 and the radiation administering device 25 may be operated to control different qualities of the incident radiation, for example, intensity, energy and duration of the incident radiation, flux density of source radiation, shape of the beam profile, and incidence direction.

A Raman scattering detecting device 27 may be arranged next to the target volume 11. The Raman scattering detecting device 27 is adapted to detect photons 29 that are induced within the target volume 11 via Raman scattering when irradiating the target volume 11 with the treatment radiation 15.

Raman scattering is a phenomenon based on non-elastic scattering of photons when photons interact with material. Raman scattering may occur at frequencies which differ from the frequency of an incident radiation. Depending on the frequency shift one can speak about anti-Stokes or Stokes scattering. Stokes scattering uses Raman scattered photons that have frequencies smaller than the frequency of an incident radiation. Anti-Stokes scattering uses Raman scattered photons that have higher frequencies than an incident radiation. A possible way to get information enhanced electromagnetic fields is to measure nonlinear effects with Raman scattering. It may be sufficient to measure an intensity of scattered radiation.

When irradiating a human or an animal body, the water volume fraction in such a body may be about 70%. The spectral shift of continuous Raman spectra for water is about 540 eV. It corresponds to the energy W [Joule]=540[eV] *1.6×10$^{-19}$ [Coulomb]. As W=h*ny, with h being the Planck constant (6.6×10$^{-34}$ Js) and ny the frequency shift, the frequency shift corresponding to the energy 540 eV is about 130 PHz. The Raman signal has to be measured at this frequency shift, and thus the Raman scattering detecting device is adapted to detect photons with this frequency shift.

For Raman scattering, devices used in Raman spectroscopy can be used to detect the Raman scattering at specific spectral lines, for example, at specific frequencies. In order to measure continuous Raman spectra the measuring can be done in a small spectral band using x-ray spectrometers. Such spectrometers are, for example, described in the article of Sun Ning, X-RAY RAMAN SPECTROSCOPY (XRS): FUNDAMENTALS AND APPLICATIONS, Literature Seminar, held on Tuesday, Oct. 9, 2007.

With the Raman scattering detecting device 27 photons 29 originating within the target volume 11 due to Raman scattering may be detected and Raman scattering data indicative thereon may be produced. These Raman scattering data may be used to control the qualities of the incident radiation. For example, Raman scattering data may be evaluated within a control unit 31 of the radiation therapy device 21. If Raman scattering data show that more Raman scattering occurred than predicted, this may indicate that it is possible to reduce the intensity of the incident radiation at the radiation source and/or the radiation administering device may be controlled accordingly. As Raman scattering depends on the local field enhancement within the target volume 11, Raman scattering data may also be used for calculating the intensity of the electromagnetic fields in the target volume 11. Depending on the calculation the radiotherapy device 21 may be controlled in order to irradiate the target volume 11 with a prescribed amount of radiation.

For example, the aim during radiotherapy may be to induce a certain intensity Fo within a diseased region which is able to damage tumor cells. If the determined near-field intensity F is larger than Fo, the power P of the source radiation can be reduced to the value P'(<P) for which F≈Fo. The human body will then receive less radiation, but still sufficient to damage tumor cells.

For example, in order to determine the prediction value, a test dose of treatment radiation may be applied and the induced Raman scattering may be measured. Once the ideal intensity of the treatment radiation coming from the radiotherapy device has been determined, radiotherapy may start and the full dose needed to irradiate the diseased region 11 adequately may be applied.

Using a Raman scattering detecting device 27, it is possible to control incident radiation 15 adequately and to use the effect of local field enhancement, even if uncertainties about the final distribution of the metal particles 17 exist and their concentration within the tumor is not known in all details.

In the absence of metal particles 17, Raman scattering may be induced used only to an extent that makes it difficult to be measurable with a Raman scattering detecting device. Nevertheless, the greatly enhanced local fields (generated by particles embedded in tumor) stimulate the Raman scattering sufficiently to make it measurable. Also the so-called surface-enhanced Raman scattering (SERS) may contribute to local field enhancement. The generated Raman scattering may directly relate to the intensities of local fields in the tumor, and thus the measured Raman intensities are a valuable source of information on induced local fields in tumor cells. Once the Raman scattering is measured, the optimum adjustment of the incident power is possible.

Figure 4:
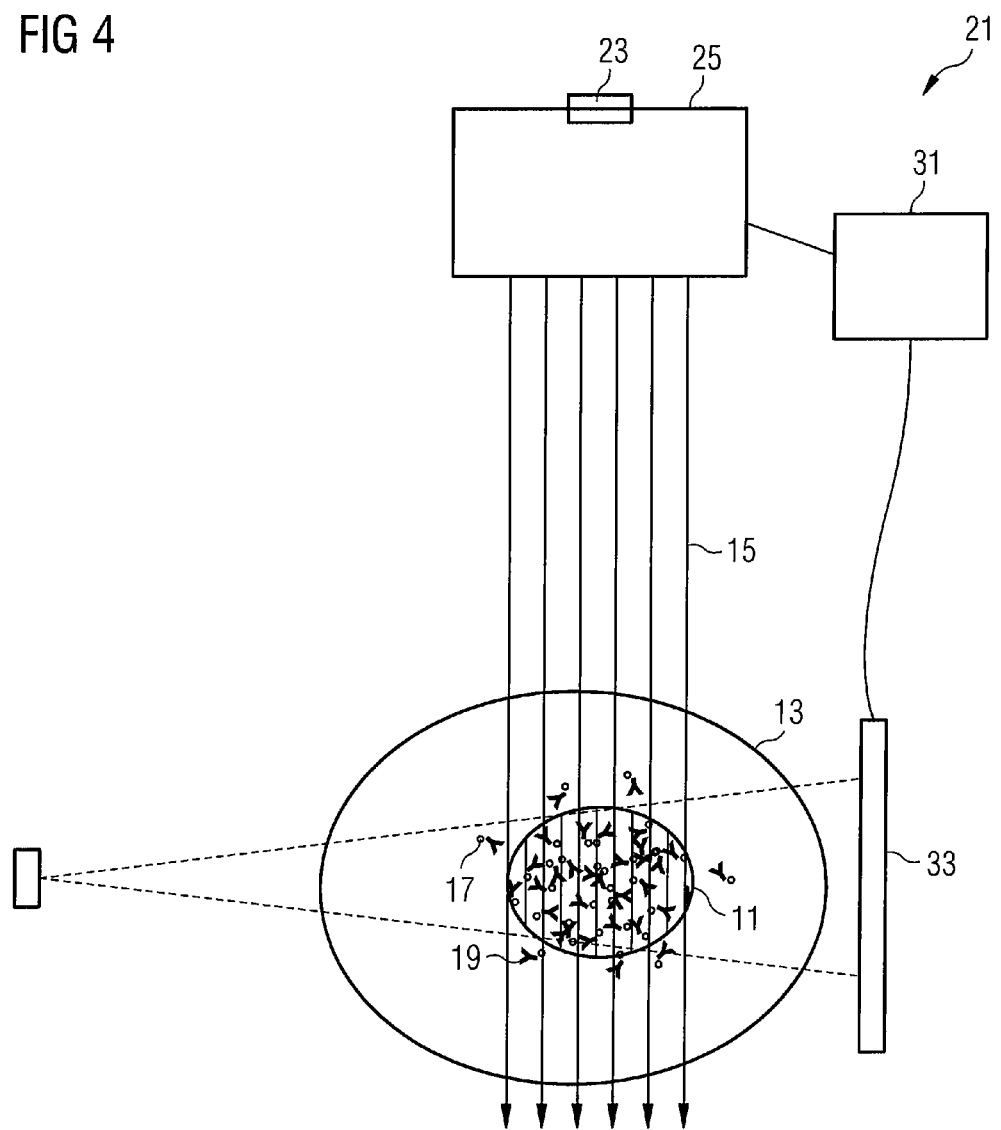
FIG. 4 shows schematically another embodiment of a radiotherapy device that can be used for an irradiation of a diseased region enriched with metal particles.

FIG. 4 shows a schematic drawing of another embodiment of a radiotherapy system 21 for treating a diseased region 11 enriched with metal particles 17. This radiotherapy device 21 differs from the radiotherapy device 21 shown in FIG. 3 and does not have a Raman scattering detecting device 27. Instead, it has a control unit 31 that is adapted to determine the local field enhancement caused by the metal particles 17 within the target volume 11. The local field enhancement may be determined by calculating the enhancement of the incident radiation taking into account parameters as the shape and size of the metal particles 17, the density and distribution of the metal particles 17 within the target volume 11, the type of the metal particles 17 and the wavelength of the incident radiation 15. The shape and size of metal particles 17 and the wavelength 15 is usually known beforehand, and the density of the metal particles 17 may be, for example, detected with a standard medical imaging device 33, for example with a computer tomography or diagnostic radiation device, schematically shown in FIG. 4.

Based on this calculation, the incident radiation 15 may be controlled in order to induce a desired intensity of radiation within the target volume 11 and in order to irradiate the target volume 11 with a predefined amount of radiation.

FIG. 5 shows a schematic diagram of invention method for performing radiation therapy. In a first act 41, vehicles with metal particles are administered to a patient's body. In a second act 43, after having waited a certain amount of time, the metal particles will have enriched within a diseased region, as the vehicles exhibit a greater affinity to the diseased region then to a healthy region. In a third act 45, based on the size of metal particles, the type of metal particles, the concentration and/or density of metal particles and/or a wavelength of the treatment radiation, the local field enhancement that occurs within the diseased region may be determined. The calculation of local field enhancement may then be used to determine control parameters that control treatment radiation that is to be applied to the diseased region, for example by controlling and adjusting the intensity of the applied treatment radiation. In a fourth act 47, the radiation treatment is started and treatment radiation is applied to the patient's body using the control parameters. In a fifth act 49, Raman scattered photons that are induced within the diseased region by applying the treatment radiation may be detected and Raman scattering data may be produced. In a sixth act 51, the detected Raman scattered photons may be used to control and/or adjust the treatment radiation applied with the radiotherapy device. For example, the Raman scattering data may be compared to predicted Raman scattering data. Additionally or alternatively, the Raman scattering data may also be used to determine or calculate the local field enhancement that occurs within the diseased region. Acts three to six may be implemented by using appropriate computer software that is installed to a computer unit of the radiotherapy device, for example.

For example, in one embodiment, a computer program product for an irradiation method for irradiating a target volume enriched with metal particles using a radiotherapy device is provided. The computer program product may include a computer usable medium comprising a computer readable program code embodied therein. The computer readable program code may be executed by a processor to determine at least one control parameter for the radiotherapy device by determining a local enhancement of a treatment radiation that is to be applied to the target volume, the local enhancement being caused due to presence of the metal particles within the target volume, and determining the control parameter based on the determined local enhancement.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A radiotherapy device, comprising:
a radiation source for producing treatment radiation,
a radiation administering device for directing the treatment radiation to a diseased region of a patient, the diseased region of the patient being enriched with metal particles,
a determining device configured for determining a value characterizing a local enhancement of the treatment radiation within the diseased region, the local enhancement being caused due to interaction of the treatment radiation with the metal particles, and
a control device configured for controlling an administration of the treatment radiation directed to the patient based on the value, the controlling being by adjusting an intensity of the treatment radiation.

2. The radiotherapy device of claim 1, wherein the determining device comprises a calculation unit configured for calculating an intensity of the locally enhanced treatment radiation within the diseased region.

3. The radiotherapy device of claim 2, wherein the calculation unit is configured to calculate the intensity of the locally enhanced treatment radiation within the diseased region using a size of the metal particles, a type of metal particles, a concentration of the metal particles, a density of metal particles and a wavelength of the treatment radiation, or any combination thereof.

4. The radiotherapy device of claim 1, wherein the control device is adapted to control a first intensity of the treatment radiation directed to the patient, such that a second intensity of the locally enhanced treatment radiation within the diseased region exceeds a predetermined value.

5. The radiotherapy device of claim 1, wherein the determining device comprises a Raman scattering detecting device configured for detecting Raman scattered photons, the Raman scattered photons originating from an irradiation of the metal particles in the diseased region with the treatment radiation, and for producing Raman scattering data.

6. The radiotherapy device of claim 5, wherein the Raman scattering detecting device is adapted for an intensity of Raman scattered photons.

7. The radiation therapy device of claim 5, wherein the radiotherapy device is configured for comparing the Raman scattering data with predicted Raman scattering data.

8. The radiation therapy device of claim 5, wherein the radiotherapy device is configured for determining a prediction value for a first intensity of the locally enhanced treatment radiation within the diseased region using the Raman scattering data.

9. The radiation therapy device of claim 8, wherein the control device is configured to control a second intensity of the treatment radiation directed to the patient when the prediction value differs from a predetermined value.

10. A method for irradiating a human or animal body, the method comprising:

administering vehicles with metal particles to a diseased region that is to be irradiated with treatment radiation, the vehicles having a higher affinity to the diseased region than to a healthy region, waiting until the diseased region is enriched with the metal particles, applying the treatment radiation to the diseased region when the diseased region is enriched with the metal particles, determining a local enhancement of the treatment radiation that is to be applied to the diseased region, the local enhancement being caused due to presence of the metal particles within the diseased region, and controlling the treatment radiation based on the local enhancement of the treatment radiation by adjusting an intensity of the treatment radiation.

11. The method of claim 10, wherein the local enhancement of the treatment radiation is determined based on a size of the metal particles, a type of metal particles, a concentration of the metal particles, a density of metal particles and a wavelength of the treatment radiation, or any combination thereof.

12. The method of claim 10, wherein the treatment radiation is adapted when the local enhancement of the treatment radiation differs from a desired local enhancement.

13. The method of claim 10, further comprising:
inducing Raman scattered photons by applying radiation to the diseased region,
detecting the Raman scattered photons and producing Raman scattering data, and
controlling the treatment radiation based on the Raman scattering data.

14. The method of claim 13, wherein the Raman scattering data are compared with predicted Raman scattering data.

15. The method of claim 14, wherein the treatment radiation is adapted when the Raman scattering data differs from the predicted Raman scattering data.

16. The method of claim 13, further comprising: predicting the local enhancement of the treatment radiation within the diseased region using the Raman scattering data.

17. The method of claim 16, wherein the treatment radiation is adapted when the predicted local enhancement differs from a desired local enhancement.

18. A computer program product for an irradiation method for irradiating a target volume enriched with metal particles using a radiotherapy device, the computer program product comprising a non-transitory computer usable medium comprising a computer readable program code embodied therein, wherein the computer program product is operable to determine at least one control parameter for the radiotherapy device by a process comprising:

determining a local enhancement of a treatment radiation that is to be applied to the target volume, the local enhancement being caused due to presence of the metal particles within the target volume, and determining the at least one control parameter based on the determined local enhancement, the at least one control parameter comprising a control parameter for controlling an intensity of the treatment radiation.

19. The computer program product of claim 18, wherein determining the local enhancement of the treatment radiation is performed using a size of the metal particles, a type of metal particles, a concentration of the metal particles, a density of metal particles and a wavelength of the treatment radiation, or any combination thereof.

20. The computer program product of claim 18, wherein the at least one control parameter is operable to adapt the treatment radiation applied to the target volume when the determined local enhancement of the treatment radiation differs from a desired local enhancement.

21. The computer program product of claim 18, wherein determining the local enhancement of the treatment radiation is performed using Raman scattering data that characterize an amount of Raman scattering occurring during irradiation of the target volume.

22. The computer program product of claim 21, wherein the at least one control parameter is operable to adapt the treatment radiation applied to the target volume if the Raman scattering data differs from a predicted Raman scattering data.

* * * * *